(12) United States Patent
Salvi et al.

(10) Patent No.: US 8,563,775 B2
(45) Date of Patent: Oct. 22, 2013

(54) PROCESS FOR THE PREPARATION OF (R)-(−)-3-(CARBAMOYLMETHYL)-5-METHYLHEXANOIC ACID AND OF PREGABALIN AND SYNTHESIS INTERMEDIATES

(75) Inventors: Annibale Salvi, Milan (IT); Antonio Nardi, Milan (IT); Bruno De Angelis, Milan (IT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 796 days.

(21) Appl. No.: 12/306,980

(22) PCT Filed: Jun. 6, 2007

(86) PCT No.: PCT/IB2007/001514
§ 371 (c)(1),
(2), (4) Date: Jan. 21, 2009

(87) PCT Pub. No.: WO2008/004044
PCT Pub. Date: Jan. 10, 2008

(65) Prior Publication Data
US 2009/0192331 A1 Jul. 30, 2009

(30) Foreign Application Priority Data
Jul. 4, 2006 (IT) .............................. MI2006A1297

(51) Int. Cl.
*C07C 205/00* (2006.01)
*C07C 207/00* (2006.01)
*C07C 229/00* (2006.01)

(52) U.S. Cl.
USPC ........................................................ 562/553

(58) Field of Classification Search
None
See application file for complete search history.

(56) References Cited

U.S. PATENT DOCUMENTS

| 5,191,112 | A  | * | 3/1993 | Nohira et al. | ................. | 562/401 |
| 5,597,848 | A  | * | 1/1997 | Ito et al. | ........................ | 514/539 |
| 5,616,793 | A  | * | 4/1997 | Huckabee et al. | ............. | 562/553 |
| 2003/0171431 | A1 | * | 9/2003 | Nakazato et al. | ............. | 514/530 |
| 2006/0211868 | A1 | * | 9/2006 | Hildbrand et al. | ............ | 548/537 |

FOREIGN PATENT DOCUMENTS

| JP | 58183669 | * 10/1983 |
| WO | 96/38405 | 12/1996 |
| WO | 01/40159 | 6/2001 |

OTHER PUBLICATIONS

Derwent abstract of Fujiwara et al. (JP 58183669).*
International Search Report for PCT/IB2007/001514, mailed Nov. 30, 2007.
Database WPI Week 198510, Derwent Publications Ltd., London, GB; AN 1985-058382, XP002459063.
Database WPI Week 200455, Derwent Publications Ltd., London, GB; AN 2004-2566017, XP002459064.
Written Opinion of the International Searching Authority for PCT/IB2007/001514, mailed Nov. 30, 2007.

* cited by examiner

*Primary Examiner* — Sudhakar Katakam
*Assistant Examiner* — Jennifer C Sawyer
(74) *Attorney, Agent, or Firm* — Nixon & Vanderhye P.C.

(57) ABSTRACT

This invention relates to the preparation of (R)-(−)-3-(carbamoylmethyl)-5-methylhexanoic acid, in particular, the resolution of the acid racemate by means of salification with optically active amines and subsequent acidification to give the (R) enantiomer of the acid; this invention also concerns the salt intermediates formed with said amines and the conversion of said (R)-(−)-3-(carbamoylmethyl)-5-methylhexanoic acid into biologically active molecules such as pregabalin.

4 Claims, No Drawings

PROCESS FOR THE PREPARATION OF (R)-(−)-3-(CARBAMOYLMETHYL)-5-METHYLHEXANOIC ACID AND OF PREGABALIN AND SYNTHESIS INTERMEDIATES

This application is the U.S. national phase of International Application No. PCT/IB2007/001514, filed 6 Jun. 2007, which designated the U.S. and claims priority to Italian Application No. MI2006A001297, filed 4 Jul. 2006, the entire contents of each of which are hereby incorporated by reference.

SUMMARY OF THE INVENTION

The present invention relates to the preparation of (R)-(−)-3-(carbamoylmethyl)-5-methylhexanoic acid, in particular the resolution of the acid racemate by means of salification with optically active amines and the isolation of the (R) enantiomer of the acid. This invention also relates to the intermediate salts formed with said amines and the conversion of said (R)-(−)-3-(carbamoylmethyl)-5-methylhexanoic acid into biologically active molecules such as pregabalin.

TECHNICAL BACKGROUND

The separation of enantiomers by means of salification with appropriate optically active counter-ions has been known for some time. However, the selection of the most suitable counter-ion and the reaction conditions, particularly the solvent and the temperature, allowing the attainment of good separation through the precipitation of one of the two diastereoisomeric salts, are difficult to predict.

(R)-(−)-3-(carbamoylmethyl)-5-methylhexanoic acid is an intermediate, useful in the preparation of biologically active molecules, such as for example pregabalin ((S)-(+)-3-(aminomethyl)-5-methylhexanoic acid).

EP0828704 describes the preparation of (R)-(−)-3-(carbamoylmethyl)-5-methylhexanoic acid by means of the salification of the acid racemate with (R)-(+)-α-phenylethylamine in chloroform, precipitation following cooling and subsequent acid hydrolysis of the salt formed between the R enantiomer of the acid and the optically active amine. The text of the patent indicates generically that the salification reaction/precipitation may proceed in an "organic solvent" but the examples normally report the use of chloroform, with the addition of a little ethanol. As is well known, chloroform is a solvent that cannot be used industrially since it is carcinogenic, even simply by inhalation.

Attempts to reproduce the described separation in a solvent other than chloroform have given negative results. In particular, crystallisation/precipitation has been attempted in solvents more suited to industrial use, such as ethyl acetate, cyclohexane, methanol, isopropanol, toluene, acetone, tetrahydrofuran and mixtures thereof, without attaining effective enantiomeric separation.

Hence, there remains a need to discover alternative synthetic pathways for the preparation of (R)-(−)-3-(carbamoylmethyl)-5-methylhexanoic acid.

DESCRIPTION OF THE INVENTION

It has now been found out that (R)-(−)-3-(carbamoylmethyl)-5-methylhexanoic acid can be obtained through the salification of 3-(carbamoylmethyl)-5-methylhexanoic acid racemate with an optically active amine suitable for enantiomeric separation, in particular, selected from 1-(1-naphthyl)ethylamine and phenylglycinol in optically active form.

Indeed, it has been found that such amines are particularly effective in the separation of the above-mentioned diastereoisomeric salts. There have been many attempts using different amines, but in the majority of cases the results have been somewhat disappointing.

Thus, according to one of the aspects thereof, the subject-matter of the present invention is a process for the preparation of (R)-(−)-3-(carbamoylmethyl)-5-methylhexanoic acid, comprising reacting 3-(carbamoylmethyl)-5-methylhexanoic acid racemate with an amine selected from 1-(1-naphthyl)ethylamine and phenylglycinol, in optically active form, in a solvent, separating the two diastereoisomeric salts and recovering the (R)-(−)-3-(carbamoylmethyl)-5-methylhexanoic acid from the corresponding salt.

3-(carbamoylmethyl)-5-methylhexanoic acid has the following formula (I)

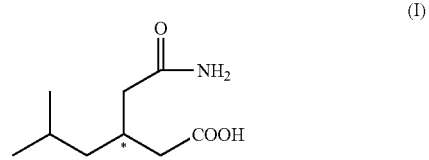

where the asterisk indicates the chiral carbon atom.

Phenylglycinol has the following formula (II)

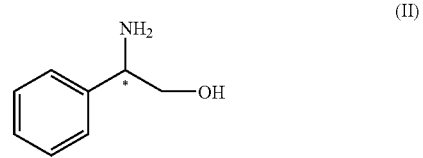

where the asterisk indicates the chiral carbon atom.

1-(1-naphthyl)ethylamine has the following formula (III)

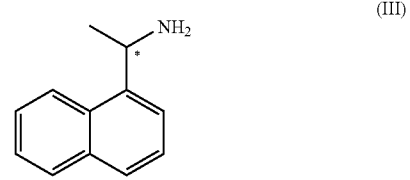

where the asterisk indicates the chiral carbon atom.

The above-indicated amines, in both (S) and (R) optically active forms, may be used for the separation of the desired enantiomer of the acid.

Unless expressly indicated otherwise, in the present description, the term "amine", used in relation to the process of the invention, refers to one of the above-indicated amines in ((S) or (R)) optically active form.

Furthermore, it has surprisingly been found that, independently of the 1-(1-naphthyl)ethylamine enantiomer used, the least soluble salt, i.e. the one which precipitates, is always that of the (S)-(+) enantiomer of the acid, i.e. the undesired enantiomer according to the present invention.

Thus, according to a first embodiment, the subject-matter of the present invention is a process for the preparation of (R)-(−)-3-(carbamoylmethyl)-5-methylhexanoic acid, comprising reacting 3-(carbamoylmethyl)-5-methylhexanoic acid racemate with an amine selected from (S)-(+)-phenylglycinol and 1-(1-naphthyl)ethylamine, the latter in any optically active form, in a solvent, precipitating and removing the precipitate consisting of the salt of the (S)-(+) enantiomer of the acid, and recovering (R)-(−)-3-(carbamoylmethyl)-5-methylhexanoic acid from the mother liquor.

According to a second embodiment, the subject-matter of the present invention is a process for the preparation of (R)-(−)-3-(carbamoylmethyl)-5-methylhexanoic acid comprising reacting 3-(carbamoylmethyl)-5-methylhexanoic acid racemate with (R)-(−)-phenylglycinol in a solvent; recovering the precipitate consisting of the salt with the (R)-(−) enantiomer of the acid; and isolating (R)-(−)-3-(carbamoylmethyl)-5-methylhexanoic acid.

Thus, alternatively, an amine selected from (R)-(+)-1-(1-naphthyl)ethylamine, (S)-(−)-1-(1-naphthyl)ethylamine, (S)-(+)-phenylglycinol and (R)-(−)-phenylglycinol may be used for the process of the present invention.

The amines (R)-(+)-1-(1-naphthyl)ethylamine and (S)-(+)-phenylglycinol are the preferred amines according to the invention.

Any solvent allowing the separation of the two enantiomers of the acid, by fractional crystallisation of the diastereoisomeric salts, may be used.

According to a preferred aspect of the invention, the solvent is an industrially acceptable solvent.

According to the present invention, by the term "industrially acceptable solvent" is meant any solvent which is not advised against for industrial use, for example, a solvent selected from ethyl acetate, alcohols such as methanol, ethanol, isopropanol, dioxane and the like, and mixtures thereof.

The selected amine is preferably used to salify at least 60% of the acid racemate used, i.e. in an amine/acid molar ratio equal to at least 0.6/1.

The quantity of solvent, or mixture of solvents, used in the initial salification is preferably comprised of between 7 and 9 ml per g of acid racemate.

The salification reaction occurs at a temperature comprised of between 25° C. and the reaction mixture reflux temperature, preferably between 50° C. and 70° C. for example, at around 65-70° C.

According to the first embodiment of the invention, the salt of the (S)-(+) enantiomer of the acid may be precipitated and removed from the mother liquor in accordance with known methods, for example by cooling and filtration.

Thus, in order to precipitate the salt of the undesired enantiomer, once the acid and the selected amine are dissolved in the solvent, the reaction mixture is cooled, for example to a temperature of approx. 10° C. or less, and the precipitating salt of the amine with the (S)-(+) enantiomer of the acid may be removed by filtration, thereby separating it from the salt of the (R) enantiomer, which remains in solution.

Once the salt of the undesired enantiomer is removed, the (R)-(−)-3-(carbamoylmethyl)-5-methylhexanoic acid salt with the amine may be recovered from the mother liquor according to conventional techniques known to those skilled in the art.

For example, the salt may be isolated so as to then liberate the free acid in accordance with known methods.

Alternatively, and according to a first preferred embodiment of the invention, the acid may be isolated from the mother liquor by extraction with water and alkali; so that the optically active amine remains in solution and the acid is extracted in a differently salified form.

Thus, according to the above-indicated first preferred embodiment, after the precipitation and removal of the salt of the undesired enantiomer, the (R)-(−) enantiomer of the acid can be recovered from the salification mother liquor by extraction with water and alkali, for example by extraction with an aqueous solution of an alkaline hydroxide, for example sodium hydroxide. The salt of the desired enantiomer of the acid with the alkaline metal in solution may then be isolated by concentration of the solution under reduced pressure. Alternatively, the free acid form of the desired enantiomer may be obtained by acidification of the alkaline solution, and filtration of the precipitate thus obtained.

According to the second embodiment, i.e. when (R)-(−)-phenylglycinol is used as the amine, the salt which precipitates is directly the desired salt, which can be isolated, for example by filtration, and from which (R)-(−)-3-(carbamoylmethyl)-5-methylhexanoic acid can be liberated according to methods known to those skilled in the art.

(R)-(−)-3-(carbamoylmethyl)-5-methylhexanoic acid may optionally be purified according to conventional techniques, for example, crystallisation in a suitable solvent.

The undesired enantiomer for pregabalin preparation may be "racemised" according to known techniques and reused according to the process of the present invention. The examples provided in the experimental section of the present description illustrate the process of the invention in detail.

The (S)-(+)-phenylglycinol salt of (R)-(−)-3-(carbamoylmethyl)-5-methylhexanoic acid and the (S)-(+)-phenylglycinol salt of (S)-(+)-3-(carbamoylmethyl)-5-methylhexanoic acid represent another subject-matter of the present invention.

The (R)-(−)-phenylglycinol salt of (R)-(−)-3-(carbamoylmethyl)-5-methylhexanoic acid and the (R)-(−)-phenylglycinol salt of (S)-(+)-3-(carbamoylmethyl)-5-methylhexanoic acid represent another subject-matter of the present invention.

The (R)-(+)-1-(1-naphthyl)ethylamine salt of (R)-(−)-3-(carbamoylmethyl)-5-methylhexanoic acid and the (R)-(+)-1-(1-naphthyl)ethylamine salt of (S)-(+)-3-(carbamoylmethyl)-5-methylhexanoic acid represent another subject-matter of the present invention.

The (S)-(−)-1-(1-naphthyl)ethylamine salt of (R)-(−)-3-(carbamoylmethyl)-5-methylhexanoic acid and the (S)-(−)-1-(1-naphthyl)ethylamine salt of (S)-(+)-3-(carbamoylmethyl)-5-methylhexanoic acid represent another subject-matter of the present invention.

As already mentioned, (R)-(−)-3-(carbamoylmethyl)-5-methylhexanoic acid is an intermediate, useful for the preparation of biologically active molecules, and for example may be converted into pregabalin ((S)-(+)-3-(aminomethyl)-5-methylhexanoic acid) through a Hoffman degradation, well known to those skilled in the art.

Thus, according to another aspect thereof, another subject-matter of the invention is a process for the preparation of pregabalin ((S)-(+)-3-(aminomethyl)-5-methylhexanoic acid) comprising a) reacting 3-(carbamoylmethyl)-5-methylhexanoic acid racemate in a solvent with an amine selected from 1-(1-naphthyl)ethylamine and phenylglycinol, in optically active form;

b) separating the two diastereoisomeric salts and recovering the (R)-(−)-3-(carbamoylmethyl)-5-methylhexanoic acid from the corresponding salt;

c) optional purifying the (R)-(−)-3-(carbamoylmethyl)-5-methylhexanoic acid by crystallisation from an organic solvent;

d) optional converting the (R)-(−)-3-(carbamoylmethyl)-5-methylhexanoic acid into pregabalin.

The above-indicated steps (a) to (d) are preferably carried out according to the previously indicated methods.

The conversion of (R)-(−)-3-(carbamoylmethyl)-5-methylhexanoic acid into pregabalin may be achieved for example by means of a Hoffmann degradation, according to reactions known to those skilled in the art.

The following examples illustrate the invention without limiting it in any manner.

EXAMPLE 1

Preparation of the (R)-(+)-1-(1-naphthyl)ethylamine salt of (S)-(+)-3-(carbamoylmethyl)-5-methlylhexanoic acid 10 g (53.4 mmoles) of 3-(carbamoylmethyl)-5-methylhexanoic acid racemate are added to a mixture of ethyl acetate (60 ml) and methanol (8 ml) at 25° C. 8.8 g (51.4 mmoles) of (R)-(+)-1-(1-naphthyl)ethylamine are added dropwise over 10 minutes in order to obtain complete dissolution. The solution is heated at reflux temperature (68° C.). The mixture is cooled slowly to 10° C. to obtain the crystallisation of the salt. The solid is filtered and washed with 30 ml of ethyl acetate. The wet product is dried at 40° C. for 6 hours giving 8 g of the (R)-(+)-1-(1-naphthyl)ethylamine salt of (S)-(+)-3-(carbamoylmethyl)-5-methylhexanoic acid as a white solid. The filtration mother liquor (approx. 80 ml) is used to obtain the desired (R)-(−)-3-(carbamoylmethyl)-5-methylhexanoic acid enantiomer.

EXAMPLE 2

Preparation of (R)-(−)-3-(carbamoylmethyl)-5-methylhexanoic acid

The mother liquor (approx. 80 ml) obtained from the filtration of the (R)-(+)-1-(1-naphthyl)ethylamine salt of (S)-(+)-3-(carbamoylmethyl)-5-methylhexanoic acid is extracted with an aqueous solution of sodium hydroxide (4.6 g of 30% sodium hydroxide diluted with 60 ml of water). The alkaline aqueous phase is further washed with 25 ml of ethyl acetate. The combined organic phases are stored (approx. 100 ml) for later recovery of the chiral amine (see example 5). The alkaline aqueous phase is concentrated under reduced pressure to give a weight of 60-65 g and then heated to 60° C. 4.3 g (39 mmoles) of 33% hydrochloric acid are added dropwise over 10 minutes to give a pH of 1-1.5. The solution is cooled slowly to 20-25° C. in order to obtain the precipitation of the crude (R)-(−)-3-(carbamoylmethyl)-5-methylhexanoic acid. The solid is filtered, washed with water and dried under reduced pressure at 50° C. for 6 hours. The solid obtained (4.5 g) is then dissolved in 54 ml of ethyl acetate at reflux temperature (76° C.); the hot solution is then filtered and cooled slowly to 25° C.

The solid precipitate is filtered and washed with 10 ml of ethyl acetate. After drying under reduced pressure at 40° C. for 6 hours, 3.2 g of (R)-(−)-3-(carbamoylmethyl)-5-methylhexanoic acid are obtained with a melting point of 132-135° C.

$[\alpha]_D = -0.5$ (C=2, methanol)

$^1$H-NMR (CDCl$_3$, 300 MHz): δ=0.93 (6H, d); δ=1.28 (2H, m); δ=1.7 (1H, m); δ=2.2-2.5 (5H, m); δ5.7 (1H, bs); δ=6.3 (1H, bs).

Enantiomeric purity: e.e.>99% (DSC)

EXAMPLE 3

Preparation of the (S)-(+)-phenylglycinol salt of (S)-(+)-3-(carbamoylmethyl)-5-methylhexanoic acid 10 g (53.4 mmoles) of 3-(carbamoylmethyl)-5-methylhexanoic acid racemate are added to a mixture of ethyl acetate (60 ml) and methanol (29 ml) at 25° C. 6.6 g (48.1 mmoles) of (S)-(+)-phenylglycinol are added and the mixture heated to reflux temperature (68° C.) to obtain complete dissolution. The mixture is cooled slowly to 25° C. to obtain the crystallisation of the salt. The solid is filtered and washed with 30 ml of ethyl acetate. The wet product is dried at 40° C. for 6 hours giving 6.1 g of the (S)-(+)-phenylglycinol salt of (S)-(+)-3-(carbamoylmethyl)-5-methylhexanoic acid as a white solid. The filtration mother liquor (approx. 80 ml) is used to obtain the desired (R)-(−)-3-(carbamoylmethyl)-5-methylhexanoic acid enantiomer.

EXAMPLE 4

Preparation of (R)-(−)-3-(carbamoylmethyl)-5-methylhexanoic acid

The mother liquor (approx. 80 ml) obtained from the filtration of the (S)-(+)-phenylglycinol salt of (S)-(+)-3-(carbamoylmethyl)-5-methylhexanoic acid is extracted with an aqueous solution of sodium hydroxide (4.5 g of 30% sodium hydroxide diluted with 60 ml of water). The alkaline aqueous phase is further washed with 30 ml of ethyl acetate. The alkaline aqueous phase is concentrated under reduced pressure to give a weight of 60-65 g and then heated to 60° C. 5 g (39 mmoles) of 33% hydrochloric acid are added dropwise over 10 minutes to give a pH of 1-1.5. The solution is cooled slowly to 20-25° C. in order to obtain the precipitation of the crude (R)-(−)-3-(carbamoylmethyl)-5-methylhexanoic acid. The solid is filtered, washed with water and dried under reduced pressure at 50° C. for 6 hours. The solid obtained (5 g) is then dissolved in 25 ml of ethyl acetate and 5 ml of methanol at reflux temperature (67° C.); the hot solution is then filtered and cooled slowly to 25° C. The solid precipitate is filtered and washed with 10 ml of ethyl acetate. After drying under reduced pressure at 40° C. for 6 hours, 2.5 g of (R)-(−)-3-(carbamoylmethyl)-5-methylhexanoic acid are obtained with a melting point of 132-135° C.

$[\alpha]_D = -0.5$ (C=2, methanol)

enantiomeric purity: e.e.>99% (DSC)

EXAMPLE 5

Preparation of the (S)-(+)-phenylglycinol salt of (R)-(−)-3-(carbamoylmethyl)-5-methylhexanoic acid The mother liquor (approx. 80 ml) obtained from the filtration of the (S)-(+)-phenylglycinol salt of (S)-(+)-3-(carbamoylmethyl)-5-methylhexanoic acid of Example 3 is concentrated to approx. ¼ of the initial volume by distillation of the solvent at atmospheric pressure. The solution is progressively cooled to 25° C.; the solid is filtered and washed with 20 ml of ethyl acetate and subsequently dried at 40° C. for 6 hours. 7 g of the (S)-(+)-phenylglycinol salt of (R)-(−)-3-(carbamoylmethyl)-5-methylhexanoic acid are obtained as a white solid.

EXAMPLE 6

Recovery of (R)-(+)-1-(1-naphthyl)ethylamine and (S)-(+)-3-(carbamoylmethyl)-5-methylhexanoic acid From examples 1 and 2 it is possible to recover the following products:

8 g of the (R)-(+)-1-(1-naphthyl)ethylamine salt of (S)-(+)-3-(carbamoylmethyl)-5-methylhexanoic acid.

the combined organic phases (approx. 100 ml)

the crude (R)-(−)-3-(carbamoylmethyl)-5-methylhexanoic acid precipitation mother liquor (aqueous acid solution)
the (R)-(−)-3-(carbamoylmethyl)-5-methylhexanoic acid crystallisation mother liquor (approx 70 ml)
and these are combined in a reaction flask.

To the mixture obtained is added 30% aqueous sodium hydroxide until the pH is >10. The two clear phases thus obtained are separated. The organic phase is filtered and evaporated to residue to give 7.5 g of recovered (R)-(+)-1-(1-naphthyl)ethylamine which can be used in the subsequent preparation. The alkaline aqueous phase is acidified with hydrochloric acid and gives a precipitate which is filtered and dried at 50° C. under reduced pressure. 5 g of (S)-(+)-3-(carbamoylmethyl)-5-methylhexanoic acid are thus obtained which can be "racemised" by acid hydrolysis to give 3-isobutyl glutaric acid. 3-isobutyl glutaric acid is the precursor of 3-(carbamoylmethyl)-5-methylhexanoic acid racemate.

EXAMPLE 7

The salts of the enantiomers of 3-(carbamoylmethyl)-5-methylhexanoic acid with optically active amines have the following characteristics.
(S)-(+)-phenylglycinol salt of (S)-(+)-3-(carbamoylmethyl)-5-methylhexanoic acid
Melting point (DSC)=160-164° C.;
$[\alpha]_D^2 = +11.7$ (C=1, methanol)
(S)-(+)-phenylglycinol salt of (R)-(−)-3-(carbamoylmethyl)-5-methylhexanoic acid
Melting point (DSC)=129-133° C.;
$[\alpha]_D^{20} = +19.4$ (C=1, methanol)
(R)-(−)-phenylglycinol salt of (S)-(+)-3-(carbamoylmethyl)-5-methylhexanoic acid
Melting point (DSC)=129-133° C.;
$[\alpha]_D^{20} = -19.3$ (C=1, methanol)
(R)-(−)-phenylglycinol salt of (R)-(−)-3-(carbamoylmethyl)-5-methylhexanoic acid
Melting point (DSC)=160-164° C.;
$[\alpha]_D^{20} = -11.5$ (C=1, methanol)
The (R)-(+)-1-(1-naphthyl)ethylamine salt of (S)-(+)-3-(carbamoylmethyl)-5-methylhexanoic acid
Melting point (DSC)=158-162° C.; $[\alpha]_D^{20} = +3.5$ (C=1, methanol)
(R)-(+)-1-(1-naphthyl)ethylamine salt of (R)-(−)-3-(carbamoylmethyl)-5-methylhexanoic acid
Melting point (DSC)=120-124° C.;
$[\alpha]_D^{20} = +11.6$ (C=1, methanol)
(S)-(−)-1-(1-naphthyl)ethylamine salt of (S)-(+)-3-(carbamoylmethyl)-5-methylhexanoic acid
Melting point (DSC)=120-124° C.;
$[\alpha]_D^{20} = -11.1$ (C=1, methanol)
(S)-(−)-1-(1-naphthyl)ethylamine salt of (R)-(−)-3-(carbamoylmethyl)-5-methylhexanoic acid
Melting point (DSC)=158-162° C.;
$[\alpha]_D^{20} = -3.2$ (C=1, methanol)

EXAMPLE 8

Preparation of the (R)-(−)-phenylglycinol salt of (R)-(−)-3-(carbamoylmethyl)-5-methylhexanoic acid in 1,4-dioxane 8 g (42.8 mmoles) of 3-(carbamoylmethyl)-5-methylhexanoic acid racemate are added to 30 ml of 1,4-dioxane at 25° C. The suspension is heated at 70° C. in order to obtain complete dissolution. Separately, a solution of 4 g (29.2 mmoles) of (R)-(−)-phenylglycinol in 50 ml of 1,4-dioxane is prepared at 70° C., which is then added dropwise to the reaction flask over approx. 10 minutes, while maintaining the temperature at 70-75° C. The mixture is heated at 90° C. until complete solution is obtained. The mixture is cooled slowly to 70° C. to obtain the crystallisation of the salt. The solid is filtered at 65-70° C. and washed with 10 ml of 1,4-dioxane. The wet product is dried at 40° C. for 6 hours giving 4.4 g of the (R)-(−)-phenylglycinol salt of (R)-(−)-3-(carbamoylmethyl)-5-methylhexanoic acid as a white solid with a melting point between 158 and 161° C.

EXAMPLE 9

Preparation of (R)-(−)-3-(carbamoylmethyl)-5-methylhexanoic acid 4.4 g (13.6 mmoles) of the (R)-(−)-phenylglycinol salt of (R)-(−)-3-(carbamoylmethyl)-5-methylhexanoic acid, obtained in Example 8, are loaded into 18 ml of water. The suspension is heated at 60° C. in order to obtain complete dissolution. 1.9 g of 33% aqueous hydrochloric acid are added dropwise while maintaining the temperature at 60-62° C. The mixture is cooled slowly to 25° C. and then maintained at this temperature for 30 minutes. The solid is filtered and washed with 4 ml of water. The wet product is dried at 40° C. for 6 hours to give 2.2 g of crude (R)-(−)-3-(carbamoylmethyl)-5-methylhexanoic acid. The solid obtained is then dissolved in 27 ml of ethyl acetate at reflux temperature; the hot solution is filtered and then cooled slowly to 25° C. The solid precipitate is filtered and washed with 5 ml of ethyl acetate. After drying under reduced pressure at 40° C. for 6 hours, 1.9 g of (R)-(−)-3-(carbamoylmethyl)-5-methylhexanoic acid are obtained with a melting point of 132-135° C.

Enantiomeric purity: e.e.>99%.

EXAMPLE 10

Preparation of (S)-(+)-3-aminomethyl-5-methylhexanoic acid (Pregabalin)

9.3 g (49.7 mmoles) of (R)-(−)-3-(carbamoylmethyl)-5-methylhexanoic acid are dissolved in 15.6 g of a 15% aqueous solution of sodium hydroxide at a temperature of 5° C. (solution A). A solution of 34.3 g (60.8 mmoles) of 13% sodium hypochlorite is prepared in 11.5 g of 30% aqueous sodium hydroxide (solution B). Solution B is added dropwise into solution A over 15 minutes, while maintaining the temperature below 20° C. Upon completion of addition the temperature of the mixture rises spontaneously up to 40-45° C. After 1 hour following addition, it is cooled to 5-10° C., and 16 g of 33% hydrochloric acid added slowly until pH 5 is reached. After stirring for 30 minutes at 5-10° C. the white solid is filtered and washed with cold water. The wet product is dried at 50° C. under reduced pressure for 6 hours. 5.7 g of crude (S)-(+)-3-aminomethyl-5-methylhexanoic acid (Pregabalin) are isolated and purified by crystallisation from a mixture of 19 g of isopropyl alcohol and 19 g of water. 4.8 g of (S)-(+)-3-aminomethyl-5-methylhexanoic acid (Pregabalin) are thus obtained with a melting point of 192-196° C.

$[\alpha]_D = +10.7$ (C=2, water)
$^1$H-NMR (D$_2$O, 300 MHz): δ=0.85 (3H, d); δ=0.87 (3H, d); δ=1.19 (2H, m); δ=1.63 (1H, m); δ=2-2.4 (3H, m); δ=2.86-3.04 (2H, m)

Enantiomeric purity: e.e.>99% (HPLC)

The invention claimed is:
1. A process for the preparation of (R)-(−)3-(carbamoylmethyl)-5-methylhexanoicacid, comprising reacting 3-(car- bamoylmethyl)-5-methylhexanoic acid racemate with an amine selected from 1-(1-naphthyl)ethylamine and phenylglycinol, in optically active form, in a solvent selected from ethyl acetate, alcohols, dioxane and mixtures thereof, separating the two diastereoisomeric salts and recovering the (R)-(−)-3-(carbamoylmethyl)-5-methylhexanoic acid from the corresponding salt.

2. The process according to claim 1, characterised in that said solvent is dioxane.

3. The process according to claim 1, characterised in that said amine is used in an amine/acid molar ratio of at least 0.6/1.

4. The process according to claim 1, comprising reacting 3-(carbamoylmethyl)-5-methylhexanoic acid racemate with (R)-(−)-phenylglycinol in a solvent; recovering the precipitate consisting of the salt with the (R)-(−) enantiomer of the acid; and isolating (R)(−)-3-(carbamoylmethyl)-5-methylhexanoic acid.

* * * * *

UNITED STATES PATENT AND TRADEMARK OFFICE
CERTIFICATE OF CORRECTION

PATENT NO.       : 8,563,775 B2                                   Page 1 of 1
APPLICATION NO. : 12/306980
DATED            : October 22, 2013
INVENTOR(S)      : Salvi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this

Fifteenth Day of September, 2015

Michelle K. Lee
*Director of the United States Patent and Trademark Office*